(12) United States Patent
Klapproth

(10) Patent No.: US 8,685,644 B2
(45) Date of Patent: Apr. 1, 2014

(54) METHOD AND DEVICE FOR DETERMINING A CONCENTRATION OF LIGANDS IN AN ANALYSED SAMPLE

(75) Inventor: Holger Klapproth, Freiburg (DE)

(73) Assignee: Endress+Hauser Conducta Gesellschaft fuer Mess- und Regeltechnik mbH+Co. KG, Gerlingen (DE)

(*) Notice: Subject to any disclaimer, the term of this patent is extended or adjusted under 35 U.S.C. 154(b) by 1353 days.

(21) Appl. No.: 10/515,535

(22) PCT Filed: Nov. 4, 2003

(86) PCT No.: PCT/EP03/12286
§ 371 (c)(1),
(2), (4) Date: Nov. 23, 2004

(87) PCT Pub. No.: WO2004/042399
PCT Pub. Date: May 21, 2004

(65) Prior Publication Data
US 2005/0239132 A1    Oct. 27, 2005

(30) Foreign Application Priority Data
Nov. 5, 2002  (DE) .................................. 102 51 757

(51) Int. Cl.
*C12Q 1/68*   (2006.01)
*G01N 33/53*  (2006.01)
*C12M 1/00*   (2006.01)
*C12M 1/34*   (2006.01)
*C12M 3/00*   (2006.01)

(52) U.S. Cl.
USPC ....... 435/6.1; 435/7.1; 435/283.1; 435/287.1; 435/287.2

(58) Field of Classification Search
USPC .............. 435/6, 6.1, 7.1, 283.1, 287.1, 287.2
See application file for complete search history.

(56) References Cited

U.S. PATENT DOCUMENTS 4,822,566 A * 4/1989 Newman ................... 422/82.01
5,807,688 A * 9/1998 Blackburn et al. ............ 435/7.6
(Continued)

FOREIGN PATENT DOCUMENTS

DE    690 29 060 T2    4/1997
DE    195 40 456 A1    5/1997
(Continued)

OTHER PUBLICATIONS

Freifelder, Physical Biochemistry, 2nd ed., Freeman and Co Publishing, New York, pp. 654-664, (1982).*
(Continued)

*Primary Examiner* — Robert T. Crow
(74) *Attorney, Agent, or Firm* — The Webb Law Firm, P.C.

(57) ABSTRACT

The invention relates to a method for determining a concentration of ligands in an analyzed sample. The inventive method consists in immobilizing receptors specifically boundable with said ligands on a support. At least one measured value of the occupation of the support surface by the receptors is determined by means of a sensor for the surface occupation. Afterwards, the sample is put in contact with the receptors. At least one measured value of the frequency of liaisons between the ligands and the receptors is determined by means of at least one detector. The concentration of ligands in the sample can be determined with the aid of the measured values of the occupation of the surface and frequency of ligands/receptors liaisons.

5 Claims, 2 Drawing Sheets

(56) References Cited

U.S. PATENT DOCUMENTS

| | | | |
|---|---|---|---|
| 6,197,503 | B1 | 3/2001 | Vo-Dinh et al. |
| 6,203,981 | B1 * | 3/2001 | Ackley et al. ............... 435/6 |
| 2001/0021534 | A1 * | 9/2001 | Wohlstadter et al. ......... 436/518 |
| 2002/0051975 | A1 | 5/2002 | Choong et al. |
| 2002/0127144 | A1 * | 9/2002 | Mehta ........................ 422/81 |
| 2002/0137056 | A1 * | 9/2002 | Erikson et al. ............... 435/6 |

FOREIGN PATENT DOCUMENTS

| | | |
|---|---|---|
| DE | 197 36 641 A1 | 3/1999 |
| DE | 100 02 566 A1 | 8/2001 |
| DE | 100 25 580 A1 | 12/2001 |

OTHER PUBLICATIONS

LeSaux et al., J. Chromatog. A, vol. 1104, pp. 352-358 (2006).*

Ding et al, Anal. Chim. Acta, vol. 543, pp. 249-253 (2005).*

The defintion of "luminescence" provided the online dictionary at thefreedictionary.com, [retrieved on Feb. 24, 2009]. Retrieved from the Internet: <www.thefreedictionary.com/luminescence>.*

Rowe-Taitt et al.; Simultaneous detection of six biohazardous agents using a planar waveguide array biosensor; Biosensors & Bioelectronics 15 (2000); pp. 579-589.

Schwerdtle R. et al., Medizinische Genetik, Berufsverband medizinishe Genetik, Munich, DE, vol. 11, No. 1 1999, pp. 29-32 (from IPER).

Database WPI Section Ch, Week 200006, Derwent Publications Ltd., London, GB; Class B04, AN 2000-072324, XP002250728 & WO 99 58137 A (Gnedoi S N), Nov. 18, 1999, Abstract.

Database WPI Section Ch, Week 199831, Derwent Publications Ltd., London, GB; Class B04, AN 1998-360617, XP002250729 & RU 2 097 061 C (Trinita Res Prodn Enterp), Nov. 27, 1997, Abstract.

Database WPI, Section Ch, Week 199645, Derwent Publications Ltd., London, GB; Class B04, AN 1996-450928, XP002250730 & JP 08 225458 A (Toray Ind Inc), Sep. 3, 1996), Abstract.

Mayr, et al., "Experimental Proof of Paraspecific Effects of Purified and Inactivated Pox Virus," *Journal of Veterinary Medicine Series B*, 36 (2): 81-99 (1989).

Ward, Michael E., "The Immunobiology and Immunopathology of Chlamydial Infections," *APMIS*, 103 (11): 769-796.

* cited by examiner

METHOD AND DEVICE FOR DETERMINING A CONCENTRATION OF LIGANDS IN AN ANALYSED SAMPLE

BACKGROUND OF THE INVENTION

1. Field of the Invention

This invention relates to a method for the determination of the concentration of ligands contained in a sample to be analyzed, whereby on at least one support, receptors are immobilized that can enter into a specific bond with the ligands, whereby the sample is brought into contact with the receptors, whereby at least one measurement value representing the frequency of the bonds between the ligands and the receptors is determined and the concentration of the ligands in the sample is determined on the basis of this measurement. The invention also relates to a device for the determination of the concentration of ligands in a sample to be analyzed, with a support, on the surface of which receptors are immobilized that, when they come into contact with the ligands, enter into a specific bond with them, and with at least one detector for the determination of at least one measurement that represents the frequency of the ligand-receptor bonds.

2. Description of the Prior Art

A method of this type and a device of this type are known from Chris A. Rowe-Taitt et al., Biosensors & Bioelectronics 15 (2000), pages 579-589. The device has, as the support, a CCD sensor on whose sensor cells antibodies are immobilized. The antibodies act as receptors which, when they come in contact with the ligands contained in the sample, bond to said ligands, as a result of which the ligand is immobilized on the CCD sensor in the form of a receptor-ligand complex. The antibodies are selected so that they are specific for the ligands, i.e. other biomolecules contained in the sample do not enter into bonds with the receptors when they come into contact with them. A biomolecule can comprise nucleic acids or derivatives thereof (DNA, RNA, PNA, LNA, oligonucleotides, plasmids, chromosomes), peptides, proteins (enzymes, proteins, oligopeptides, cellular receptor proteins and their complexes, peptide hormones, antibodies and fragments thereof, carbohydrates and their derivatives, in particular glycolized proteins and glycosides, fats, fatty acids and/or lipids. After the sample has been brought into contact with the receptors and the ligand has bonded to the receptors, a fluid is applied to the CCD sensor which contains antibodies marked with a fluorescent agent. The antibodies bond to the ligands, as a result of which the ligands are marked with the fluorescent agent. In a further step, the sensor surface with the receptor-ligand complexes immobilized on it is washed to remove the antibodies marked with the fluorescent agent that are not bonded to a receptor from the sensor surface. Then the fluorescent agent is irradiated with optical excitation radiation to excite the emission of fluorescent radiation. The fluorescent radiation thereby released is measured by means of the optical detectors of the CCD sensor. It represents a measurement of the frequency of the ligand-receptor bonds and thus of the concentration of the ligands in the sample.

To make possible a quantitative determination of the concentration of the ligands in the sample, the device must be calibrated. In a calibration method known from actual practice, for this purpose first a dilution series is produced that has a number of calibration samples that contain the ligands in different known concentrations. This can be done, for example, by weighing the ligands, then mixing them with a known quantity of fluid and producing different dilutions from the mixture. To take the calibration measurement, a number of the above mentioned devices for the determination of the concentration of the ligands corresponding to the number of the calibration samples is prepared, whereby it is assumed that these devices are identical to one another and identical to the device used for the actual concentration measurement. By means of these devices, the calibration samples and analyzed, whereby for each of the individual calibration samples, one measurement is taken for the intensity of the fluorescent radiation. In this manner, for each calibration sample a value pair is obtained, consisting of the known concentration of the ligand in the calibration sample and the intensity of the fluorescent radiation measured for this concentration. By means of this value pair, a calibration curve is prepared for which the value pairs form interpolation nodes.

The calibration has the disadvantage that a number of devices that equals the number of calibration samples is required, and these devices can then no longer be used for the measurement of the sample to be analyzed. The calibration of the device is therefore complex and expensive. Another disadvantage of this known method is that for the calibration curve, there are measurements only at the interpolation nodes, and that the profile of the calibration curve between the interpolation nodes must be estimated by interpolation, for example. Finally, however, it is also a problem that the receptors can be unstable, as a result of which the concentration of the receptors that are immobilized on the carrier varies over time. The calibration measurements and the measurement on the sample to be analyzed must therefore be performed as simultaneously as possible, which further complicates the method.

DE 197 36 641 A1 also describes a method of the type described above, in which first a blind measurement is made in which receptors that are immobilized on a silanized glass support are brought into contact with a peroxidase tracer without analyte. From the blind measurement, a measurement for the number of bonding events is determined. This number is significantly lower than the number of receptors that are immobilized on the support, because the peroxidase tracer has a higher molecular weight than the receptors. In addition, calibration solutions of various concentrations are produced that cover the entire measurement range. With these calibration solutions, calibration measurements are measured from which calibration curves are prepared with the value measured in the blind measurement. then the device is regenerated by bringing the receptors that are immobilized on the support with an acid solution, which breaks the bonds between the receptors and the peroxidase tracer. Then the receptors are brought into contact with the sample and measurement values are determined for the frequency of the bonds between the ligands and the receptors. By means of these measurement values and the calibration curves, the concentration of the ligands in the sample is determined. The method has the disadvantage that the receptors can be damaged by contact with the acid solution, as a result of which measurement errors can occur. It is also disadvantageous that the method is relatively time-consuming, because during the calibration, the user has to wait until the bonds between the receptors and the peroxidase tracer have been formed, and the device also has to be regenerated.

The object of the invention is therefore to create a method and a device of the type described above which make it possible to easily determine the concentration of a ligand contained in a sample to be analyzed.

SUMMARY OF THE INVENTION

With reference to the method, the invention teaches that this object can be accomplished by the method claimed by the invention, in which at least one measurement value is determined for the surface occupation of the surface of the carrier with the receptors, and the concentration of the ligands is determined by means of the measurement values for the surface occupation and the frequency of the bonds.

With reference to the device, the invention teaches that this object can be accomplished by the device which has at least one surface occupation sensor for the measurement of the surface occupation of the surface of the carrier with the receptors, and the surface occupation sensor and the detector are connected with an evaluation device for the determination of the concentration of the ligands in the sample.

It is thereby advantageously possible, by the corresponding application of the law of mass action of the ligand concentration in the sample to perform the following simple calculation:

$$\text{Ligand concentration} = K \frac{M}{F}$$

In the equation, M represents the measured value for the frequency of the bonds between the ligands and the receptors that are immobilized on the support, in other words for the concentration of the receptor-ligand complexes that are immobilized on the support. F is the measured value for the surface occupation of the surface of the support with the receptors and K is a bonding constant, which can be determined experimentally, for example. The term "surface occupation" in this case means the number of receptors that are immobilized on the support per unit of surface area of the support. The surface occupation of the surface of the support with the receptors is preferably conducted immediately before the sample to be analyzed is place in contact with the receptors. Even with unstable receptors, therefore, the concentration of the ligands in the sample can be determined with great accuracy on the basis of the measurement value or the measurement values for the frequency of the actual bonds between the ligands and the receptors that are present in the surface occupation on the support. The method and the device claimed by the invention therefore make it possible, without a complex and time-consuming preparation and analysis of a dilution series, to measure the concentration of the ligands in the sample with great precision. In contrast to a blind measurement, in the measurement of the surface occupation it is not the number of bonding events per unit of surface area that is measured, but the number of receptors per unit of surface area. The latter is determined as a measurement for the sensitivity of the device. The surface occupation is important primarily for the dynamics of the measurement. It has been shown, for example, that with increasing surface occupation, i.e. with increasing density of the receptors, the probability that a ligand will bond to a receptor increases. This relationship results from the fact that the bonding event can only take place if the ligand is in the immediate vicinity of a receptor.

In one advantageous configuration of the method, the receptors are not bonded to ligands during the measurement of the surface occupation, and the sample is brought into contact with the receptors only after the surface occupation of the surface of the support with the receptors has been determined. It is thereby possible to determine the surface occupation with greater accuracy.

In one advantageous realization of the invention, the at least one surface occupation sensor is an impedance sensor. After the immobilization of the receptors on the surface of the support, for the determination of the measurement value for the surface occupation, first the electrical impedance on the surface of the carrier is measured. Then the sample is brought into contact with the receptors and the at least one measurement value for the frequency of the bondings is determined. The impedance sensor can in particular be realized in the form of a capacitance, between the electrodes of which an alternating electromagnetic field is applied. The receptors thereby act as a dielectric, the presence of which influences the electrical capacitance of the capacitor. The capacitor can be part of an oscillator circuit, the resonance or oscillation frequency of which is measured to determine the surface occupation of the support by means of a suitable measurement instrument.

In one preferred embodiment of the invention, the at least one surface occupation sensor is a field effect transistor, whereby the support is preferably a semiconductor substrate into which the field effect transistor is integrated. The support is therefore realized in the form of a semiconductor chip into which the at least one surface occupation sensor and optionally the at-least one detector can be economically integrated for the measurement of the value that represents the frequency of the ligand-receptor bonds. After the immobilization of the receptors on the surface of the support, first the electrical field strength on the surface of the support is measured to determine the measurement value for the surface occupation. Then the sample is brought into contact with the receptors and the at least one measurement value for the frequency of the bonding is determined.

In one advantageous realization of the invention, the device for the excitation of the emission of luminescent radiation as a function of the bonding of the ligand to the receptor has at least one optical radiation source, in the radiation range of which the receptors are located, whereby the at least one detector is realized to detect the luminescent radiation in the form of a radiation receiver, which is preferably integrated into the semiconductor substrate of the support. The receptor-ligand complexes that are immobilized on the surface of the carrier can then be marked directly or indirectly by means of an antibody or similar biomolecule with a luminescent agent. It is also conceivable, however, that the ligand itself can be excited by the radiation source to emit luminescence. Finally, the concentration or the frequency of the receptor-ligand complexes can also be determined by bringing, during and/or after contact has been established between the ligands and the receptors, a competitor into contact with receptors, which is marked directly or indirectly with a luminescent agent, the luminescent radiation of which is measured by means of at least one detector.

It is particularly advantageous if a plurality of detectors are integrated in a matrix pattern into the semiconductor substrate, and if a plurality of surface occupation sensors are distributed over this matrix, preferably between the detectors. It is thereby possible, among other things, for the detectors and the surface occupation sensors to be located in alternation on the surface of the support. In that case, the device can be used for a measurement of the concentration of the ligands in the sample with a high degree of local resolution.

One exemplary embodiment of the invention is illustrated in greater detail below with reference to the accompanying drawings, some of which are merely schematic:

DETAILED DESCRIPTION OF THE PREFERRED EMBODIMENTS

Figure 1:
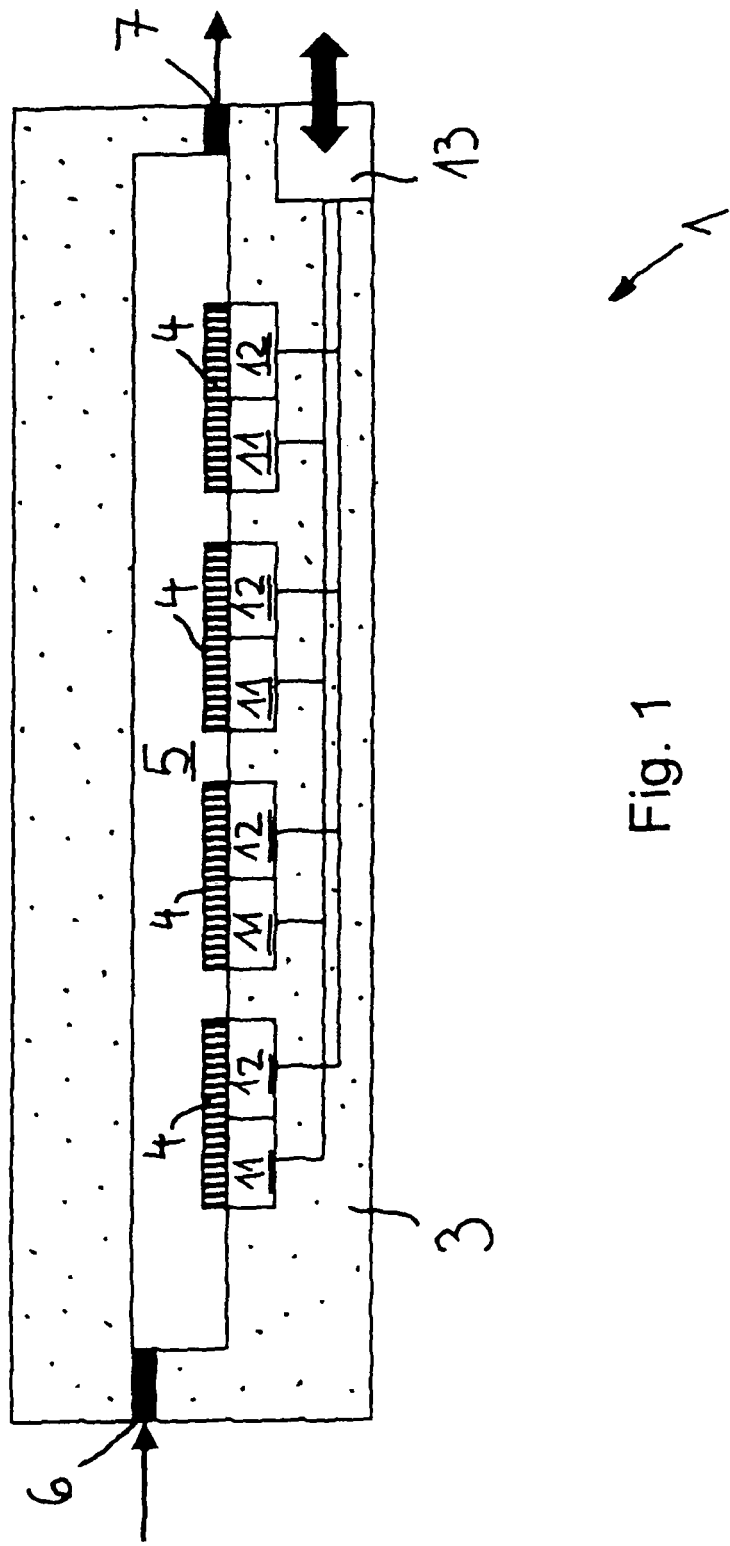
FIG. 1 is a cross section through a device for the determination of the concentration of ligands contained in a sample to be analyzed, whereby the device is realized in the form of a flow cell.

A device identified overall as 1 for the determination of the concentration of ligands 2 contained in a sample to be analyzed has the support 3, on the surface of which biological antibodies in the form of receptors 4 are immobilized which form a single layer on the support 3. The immobilization of the receptors 4 can be achieved, for example, by a silanization or a polyimide layer located on the surface of the support 3, to which the receptors 4 adhere. The receptors 4 can be imprinted on the support 3 or on the polyimide layer on the support 3. As shown in FIG. 1, on the surface of the support 3 there are a plurality of measurement points with receptors 4 that are at some distance from one another.

The support 3 is formed by a wall area of a flow-through measurement chamber which has an interior cavity 5 with an inlet opening 6 and an outlet opening 7 for the sample. As shown in FIG. 1, the receptors 4 are located on the inside of the support 3 facing the interior cavity 5. For the determination of the concentration of the ligands 2 in the sample, the sample is introduced by means of a delivery device through the inlet opening 6 into the interior cavity 5 of the measurement chamber, whereupon the ligands 2 come in contact with the receptors 4.

Figure 2:
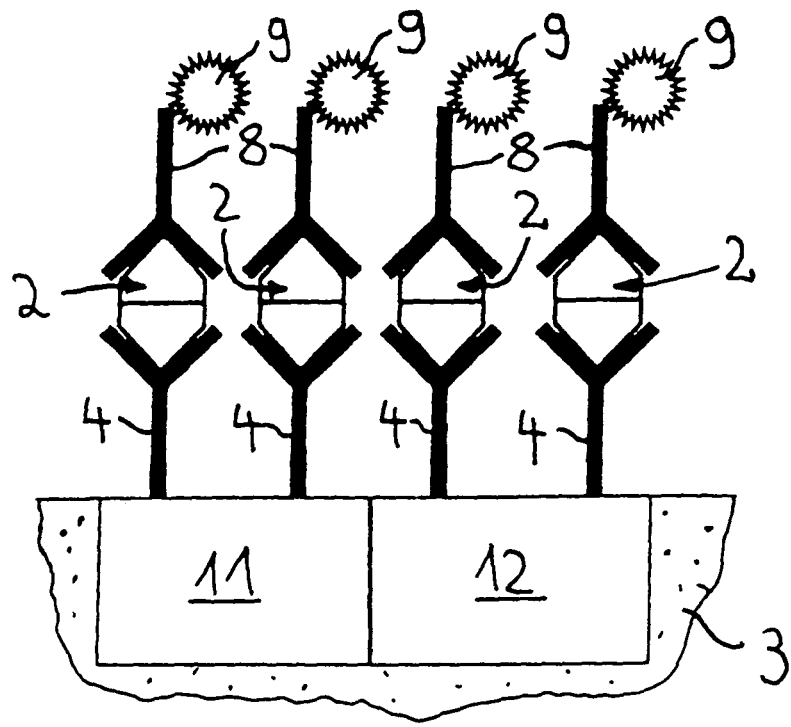
FIG. 2 is a partial section through the wall area of the flow cell, which has a detector for the detection of ligand-receptor complexes located on the surface of the wall area and a surface occupation sensor for the measurement of the surface of the wall area covered by the receptors.
Figure 3:
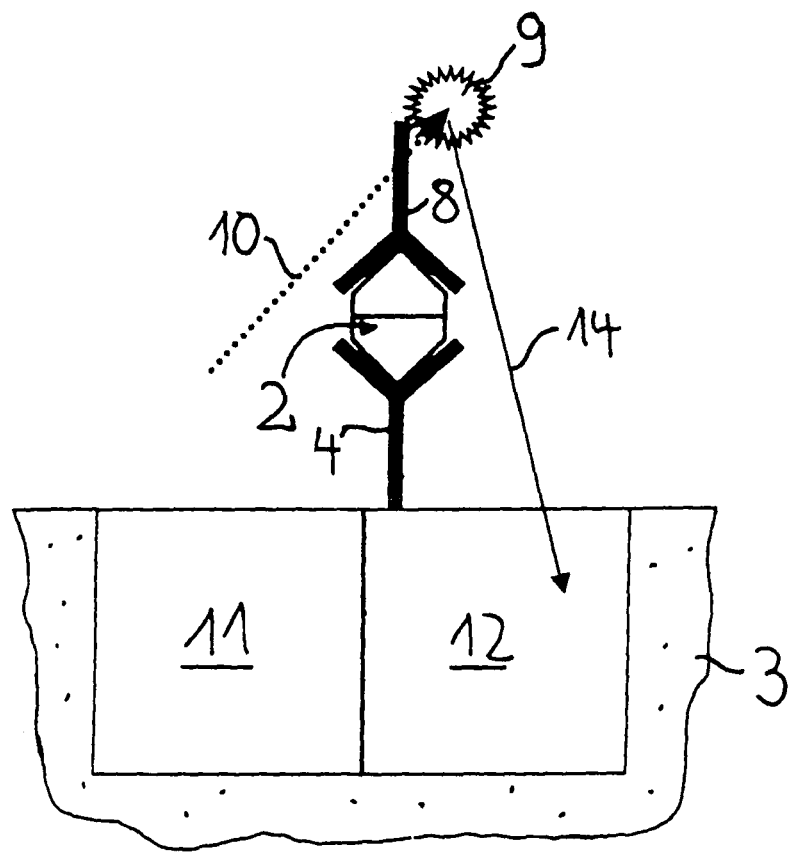
FIG. 3 is an illustration like the one in FIG. 2, whereby the receptor-ligand complex is marked with a luminescent agent which is excited by means of exciter radiation to emit luminescent radiation.

The ligands 2 have epitopes that enter into a specific bond when they come into contact with the receptors 4. The ligands 2 are thereby immobilized on the support 3 in the form of a receptor-ligand complex, as illustrated schematically in FIGS. 2 and 3.

Secondary antibodies 8 that are marked with a luminescent agent 9 are brought into contact with the ligands 2. The secondary antibodies 8 bond to the epitopes of the ligands 2, as a result of which the receptor-ligand complexes are marked with the luminescent agent 9. It is also conceivable, however, that the receptor-ligand complexes can themselves be luminescent, for example as a result of chemiluminescence. In that case, the marking of the receptor-ligand complexes with the luminescent agent 9 can optionally be omitted.

In an additional step, the support 3 is washed to remove the components of the sample that are not bonded to a receptor 4. For example, through the inlet opening 6 a flushing fluid can be introduced into the interior cavity, by means of which the components of the sample not immobilized on the support can be flushed out of the interior cavity 5 via the outlet opening 7.

Then the luminescent substance 8 that is still bonded to the receptors 4 is irradiated with an exciter radiation 10 using a radiation source that is not shown in any further detail in the drawing. The spectrum of the exciter radiation 10 has at least one excitation wavelength at which the luminescent substance 9 is excited to emit luminescent radiation 14.

The support 3 has a semiconductor substrate into which detectors 11 are integrated, which are realized in the form of optical radiation receivers, for example in the form of photodiodes, for the measurement of the luminescent radiation 14. The detectors 8 are arranged in a matrix pattern in a plurality of rows and columns. By means of the detectors 8, measurements with some degree of local resolution are recorded which represent a measurement of the number of the receptor-ligand complexes per unit of surface area of the support 3.

To measure the surface occupation of the surface of the support 3 with the receptors 4, surface occupation sensors 12 are integrated into the semiconductor substrate of the support 3. The surface occupation sensors 12 are realized in the form of field effect transistors (FET), the gate of which, for the detection of the receptors 4, is located on the surface of the support 3 or in a layer of the support 3 close to the surface, so that the receptors 4 immobilized on the support come into electrical contact with the gate. FIG. 1 shows that the surface occupation sensors 12 and the detectors 8 are located next to one another in alternation, and that for each measurement point formed by a receptor area there is at least one surface occupation sensor 12 and at least one detector 8. The measurement of the surface occupation of the support surface with the receptors 4 is preferably taken immediately before the sample is brought into contact with the receptors 4. It is thereby assumed that the surface occupation between this measurement and the determination of the frequency or concentration of the receptor-ligand complexes by the measurement of the luminescent radiation 14 varies not at all or only insignificantly. The measurement value for the surface occupation represents a yardstick for the number of receptors 4 per unit of support surface area.

For the determination of the concentration of ligands 2 in the sample, the surface occupation sensors 12 and the detectors 8 are connected with an evaluation device 13 which, in the exemplary embodiment illustrated in FIG. 1, is integrated into the support 3. By means of the evaluation device 13, the concentration of ligands 2 is determined from a measurement value M which represents the frequency of the receptor-ligand complexes, a measurement value F for the surface occupation of the surface of the support 3 with the receptors 4 and a bonding constant K, as follows:

$$\text{Ligand concentration} = K \frac{M}{F}$$

It is thereby even possible to determine the concentration of the ligands 2 for individual measurement points or for groups of a plurality of measurement points separately, so that overall, a one-dimensional or even two-dimensional concentration measurement with some degree of local resolution can be conducted.

The evaluation device 13 has an interface device which is shown only schematically in the drawing for connection with a higher-level display and/or analysis unit, such as a microcomputer, for example. The display can provide a graphic presentation of the measurement values for the surface occupation, the luminescent radiation 14 and/or the concentrations of the ligands 2 which can be calculated from those data.

In the method for the determination of the concentration of ligands 2 contained in a sample to be analyzed, therefore, receptors 4 that can enter into a specific bond are immobilized on a support 3. By means of at least one surface occupation sensor 12, at least one measurement value is determined for the surface occupation of the surface occupation of the surface of the support 3 with the receptors 4. Then the sample is brought into contact with the receptors 4. By means of at least one detector 11, at least one measurement value that represents the frequency of the bonds between the ligands 2 and the receptors 4 is determined. The concentration of the ligands 2 in the sample is determined on the basis of the measurement values for the surface occupation and the frequency of the ligand-receptor bonds.

The invention claimed is:

1. Method for the determination of the concentration of ligands contained in a sample to be analyzed, comprising the steps of, immobilizing on a support receptors that can enter into a specific bond with the ligands, bringing the sample into contact with the receptors, obtaining at least one measurement value representing the frequency of the bonds between the ligands and the receptors, and determining on the basis of this measurement value the concentration of the ligands in the sample, wherein at least one measurement value of the surface occupation of the surface of the support with the receptors is determined, and that the concentration of the ligands is determined by means of the measurement values for the surface occupation and the frequency of the bonds;

wherein the receptors are not bonded to ligands during the measurement of the surface occupation, and that the sample is brought into contact with the receptors after the surface occupation of the surface of the support with the receptors has been determined;

wherein after the immobilization of the receptors on the surface of the support, for the determination of the measurement value for the surface occupation, the electrical impedance is measured on the surface of the support, and that then the sample is brought into contact with the receptors and the at least one measurement value for the frequency of the bonds is determined, and wherein the at least one measurement value for the frequency of the bonds between the ligands and receptors is determined by a luminescent radiation method wherein luminescent radiation is activated by an optical radiation source and wherein the concentration of ligands is determined by the formula:

$$\text{Ligand concentration} = K(M/F)$$

wherein M represents the frequency of the receptor ligand complexes, F represents the surface occupation of the surface of the support with the receptors, and K is the bonding constant, further wherein said support is a semiconductor substrate comprising a plurality of detectors and a plurality of surface occupation sensors together arranged in a matrix pattern comprising an alternating pattern of said plurality of detectors and said plurality of surface occupation sensors, whereby each measurement point formed by each receptor comprises therebelow at least one detector and at least one surface occupation sensor, said plurality of detectors being used to obtain at least one measurement value representing the frequency of the bonds between the ligands and the receptors.

2. The method of claim 1, wherein after the immobilization of the receptors on the surface of the support for the determination of the measurement value for the surface occupation, the electrical field strength on the surface of the support is measured, and that then the sample is brought into contact with the receptors and the at least one measurement value for the frequency of the bonds is determined.

3. The method of claim 1, wherein the electrical impedance used for the determination of the measurement value for the surface occupation of the surface of the support with the receptors is measured before the sample is brought into contact with the receptors.

4. The method of claim 1, wherein each detector is adjacent to one surface occupation sensor, and said plurality of detectors and said plurality of surface occupation sensors together form a plurality of detector—surface occupation sensor pairs.

5. The method of claim 1, wherein the measurement of the surface occupation is performed immediately before the sample is brought into contact with the receptors.

* * * * *

UNITED STATES PATENT AND TRADEMARK OFFICE
CERTIFICATE OF CORRECTION

PATENT NO.        : 8,685,644 B2                                            Page 1 of 1
APPLICATION NO.   : 10/515535
DATED             : April 1, 2014
INVENTOR(S)       : Holger Klapproth It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1483 days.

Signed and Sealed this
Twenty-ninth Day of September, 2015

Michelle K. Lee
*Director of the United States Patent and Trademark Office*